United States Patent [19]

Uchinami et al.

[11] Patent Number: 4,958,611
[45] Date of Patent: Sep. 25, 1990

[54] AIR-FUEL RATIO CONTROLLER OF INTERNAL COMBUSTION ENGINE

[75] Inventors: Masanobu Uchinami; Toshihisa Takahashi, both of Himeji; Hitoshi Inoue, Amagasaki; Takahiro Moronaga; Shinichi Nishida, both of Himeji, all of Japan

[73] Assignee: Mitsubishi Denki Kabushiki Kaisha, Tokyo, Japan

[21] Appl. No.: 317,486

[22] Filed: Mar. 1, 1989

[30] Foreign Application Priority Data

Mar. 1, 1988 [JP] Japan .................. 63-49085

[51] Int. Cl.⁵ ............................. F02D 41/22
[52] U.S. Cl. ................... 123/479; 123/489; 204/401
[58] Field of Search ............ 123/479, 440, 489; 204/401, 406

[56] References Cited

U.S. PATENT DOCUMENTS

| | | | |
|---|---|---|---|
| 4,706,633 | 11/1987 | Nakagawa | 123/440 |
| 4,707,241 | 11/1987 | Nakagawa et al. | 123/440 |
| 4,708,777 | 11/1987 | Kuraoka | 123/440 |
| 4,715,343 | 12/1987 | Kinoshita | 123/440 |
| 4,721,084 | 1/1988 | Kawanabe et al. | 123/489 |
| 4,724,814 | 2/1988 | Mieno et al. | 123/479 |
| 4,724,815 | 2/1988 | Mieno et al. | 123/489 |
| 4,765,298 | 8/1988 | Kojima et al. | 123/440 |
| 4,777,922 | 10/1988 | Mieno et al. | 123/479 |
| 4,819,602 | 4/1989 | Mieno et al. | 123/479 |

FOREIGN PATENT DOCUMENTS

| | | | |
|---|---|---|---|
| 0005417 | 1/1980 | Japan | 123/440 |
| 35347 | 2/1986 | Japan . | |
| 44272 | 3/1987 | Japan . | |

*Primary Examiner*—Tony M. Argenbright
*Assistant Examiner*—Robert E. Mates
*Attorney, Agent, or Firm*—Sughrue, Mion, Zinn, Macpeak & Seas

[57] ABSTRACT

The air-fuel (A/F) ratio controller of an internal combustion engine related to the invention detects occurrence of abnormal condition in a heater on the basis of the resistance value of this heater which heats an oxygen sensor generating a specific voltage responsive to the difference of oxygen concentration between atmosphere and exhaust gas of the engine and of an oxygen pump allowing the pump current flow in order that the voltage can be the predetermined value. If abnormal condition arises in the heater, the A/F ratio controller stops fuel feedback control operation. The A/F ratio controller related to the invention forms a Wheatstone bridge circuit which includes the heater mentioned above and detects occurrence of an abnormal condition in the heater on the basis of the equilibrium condition of signal outputted from the Wheatstone bridge circuit.

1 Claim, 6 Drawing Sheets

AIR-FUEL RATIO CONTROLLER OF INTERNAL COMBUSTION ENGINE

BACKGROUND OF THE INVENTION

1. Field of the Invention

The present invention relates to a device for controlling the air-fuel (A/F) ratio of an internal combustion engine, more particularly, to an air-fuel ratio controller which stops control of air-fuel ratio when an abnormal condition occurs in the heater which heats an oxygen sensor detecting oxygen concentration of exhaust gas and an oxygen pump in order to maintain activity of these.

2. Description of the Prior Art

According to the art proposed by Japanese Utility Model Application Laid-Open No. 62-18659 (1987), using a wide-range air-fuel ratio sensor composed of an oxygen sensor generating electromotive force responsive to the difference of oxygen concentration between atmosphere and exhaust gas from an internal combustion engine and an oxygen pump allowing pump current flow for taking oxygen into and out of exhaust gas for comparison with atmosphere, pump current is controlled in order that voltage outputted from the oxygen sensor can be a predetermined value. The proposed air-fuel ratio sensor detects the air-fuel ratio of the engine according to the magnitude of pump current. The air-fuel ratio sensor proposed by the above art can continuously measure the air-fuel ratio from rich to lean degree. FIG. 1 is a schematic block diagram of the heater circuit of the wide-range air-fuel ratio sensor cited above. Heater 87 heats the wide-range A/F ratio sensor 80 so that it can be held at the predetermined temperature, and thus, the A/F ratio sensor 80 is activated and correctly functions itself.

Nevertheless, the A/F ratio sensor 80 proposed by the above art has a simplified constitution in which the heater 87 is connected between battery 37 and the ground. As a result, it cannot detect failure in the supply of voltage to the heater 87 caused by insufficient contact of connectors for example. If the heater 87 malfunctions as a result of disconnection, a signal outputted from the A/F ratio sensor 80 deviates to the lean side.

If the fuel control system executes fuel feedback control operation in reliance on the value delivered from a faulty sensor, the actual air-fuel ratio deviates to the richer side than the objective value. This in turn lowers the driving characteristic and generates an inadequately combusted exhaust gas which may cause fire or trouble to occur in the engine.

SUMMARY OF THE INVENTION

The invention has been achieved to fully solve the problems mentioned above.

A primary object of the invention is to provide a novel device for precisely controlling the air-fuel ratio of an internal combustion engine, which securely detects an abnormal condition present in the heater on the basis of the resistance value of an oxygen sensor and heater of an oxygen pump, and then, if the heater abnormally functions, it stops the operation for controlling the air-fuel ratio to prevent degradation of driving characteristic, occurrence of inadequately combusted exhaust gas, fire or problems in the engine itself.

A second object of the invention is to provide a novel device for precisely controlling the air-fuel ratio of an internal combustion engine, which incorporates a Wheatstone bridge circuit including the heater of the oxygen pump and detects whether the equilibrium of signals outputted from the Wheatstone bridge circuit deviates by more than a predetermined value, or not. This permits the air-fuel ratio controller to securely detect an abnormal condition present in the heater by detecting the value deviated from equilibrium by more than the predetermined value.

The above and further objects and features of the invention will be more fully apparent from the following detailed description with accompanying drawings.

DESCRIPTION OF THE PREFERRED EMBODIMENTS

Referring now more particularly to the accompanying drawings, a preferred embodiment of the A/F ratio controller related to the invention is described below.

Figure 1:
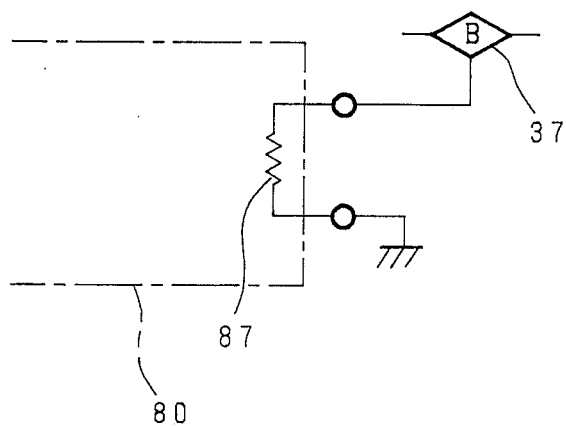
FIG. 1 is a simplified block diagram of the heater circuit of a conventional air-fuel ratio control device.
Figure 2:
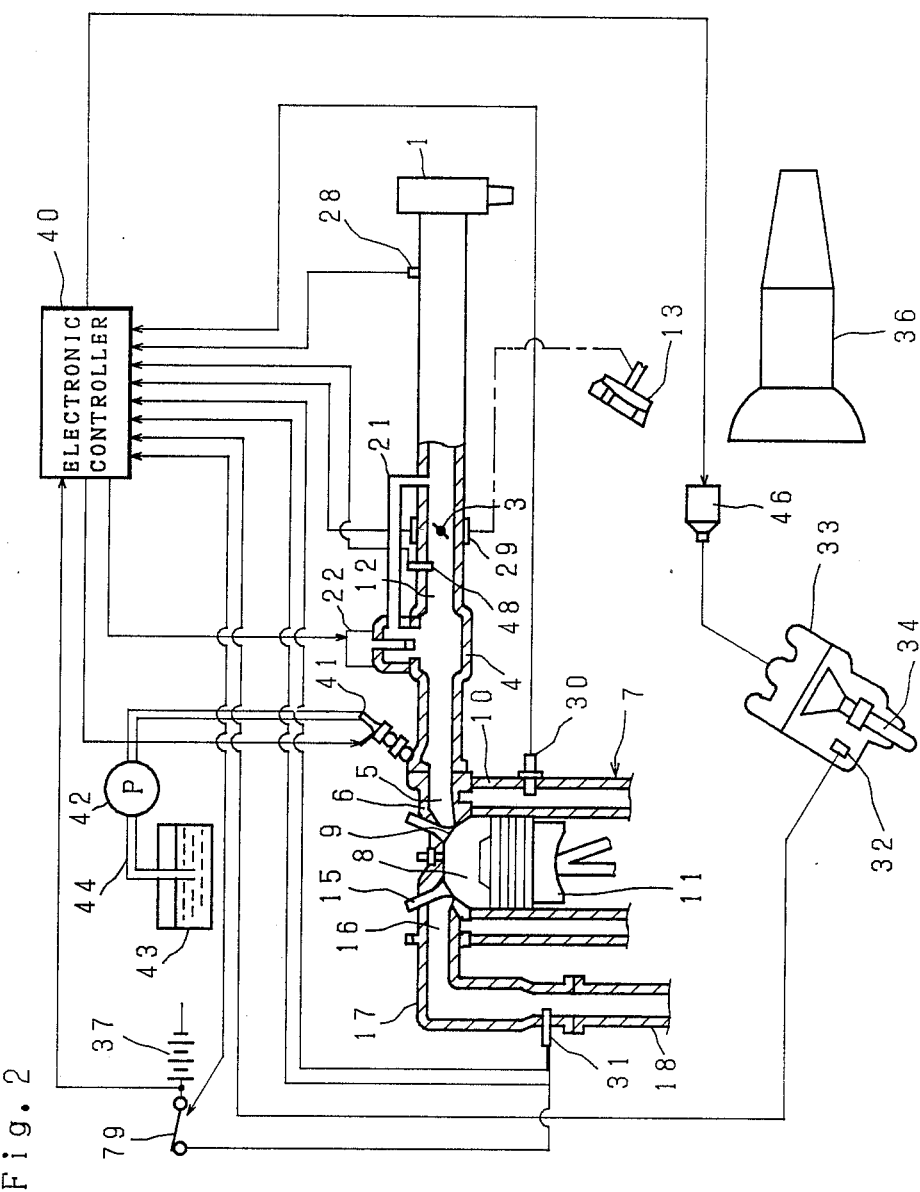
FIG. 2 is a schematic block diagram of the air-fuel ratio controller according to the invention.

FIG. 2 is a schematic block diagram of the A/F ratio controller according to the invention. Fresh air absorbed by air-cleaner 1 is delivered to combustion chamber 8 of the engine 7 through throttle valve 3, surge tank 4, air-inlet port 5, and air-passage 12 having air-inlet valve 6. Air-passage 12 incorporates negative-pressure sensor 48 which is connected to the electronic controller 40. Throttle valve 3 interlinks itself with accelerator 13 in front of the driver's seat. Combustion chamber 8 is sectioned by cylinder head 9, cylinder block 10, and piston 11. Exhaust gas generated by combustion of the fuel-mixed vapor is discharged into atmosphere through exhaust valve 15, exhaust port 16, multiple exhaust tubes 17, and final exhaust tube 18. The upper stream of throttle valve 3 is connected to the surge tank 4 via bypass 21. Bypass-flow control valve 22 maintains the speed of the rotation of the engine constant during idling mode by controlling flow-sectional area of bypass 21. Absorbed-air temperature sensor 28 installed inside of air-passage 12 detects the temperature of absorbed air. Throttle-position sensor 29 detects the aperture degree of throttle valve 3. Radiated-water temperature sensor 30 installed on cylinder block 10 detects temperature of radiated water. The A/F ratio detection device 31 is installed on the assembled portion of multiple-exhaust tubes 17 and connected to battery 37 via switch 79 for detecting the air-fuel ratio at the assembled portion of the multiple exhaust tubes 17. Crank-angle sensor 32 detects the crank angle and the number of the rotation of crank shaft by checking the rotation of shaft 34 of distributor 33 which is connected to the crank shaft of the engine 7. The reference numeral 36 designates the transmission unit.

Signals outputted from absorbed-air temperature sensor 28, throttle-position sensor 29, radiated-water temperature sensor 30, battery 37, negative-pressure sensor 48, A/F ratio detection device 31, and crank-angle sensor 32, are respectively delivered to the electronic controller 40. Fuel injection valve 41 is installed at a position close to a plurality of air-inlet ports 5 so that it can deal with a plurality of cylinders respectively. Pump 42 feeds fuel from fuel tank 43 to the fuel injection pump 41 via fuel passage 44. Using signals from the sensors mentioned above as parameters, the electronic controller 40 computes the quantity of fuel to be jetted, and then outputs electric pulses each having a specific width corresponding to the computed quantity of fuel to be jetted. In response to the received pulse-width signal, the fuel injection valve 41 opens itself for jetting fuel.

The electronic controller 40 controls operations of by-pass-flow-quantity control valve 22 and ignition coils 46. Secondary coils of these ignition coils 46 are respectively connected to the distributor 33.

The electronically-controlled fuel injection system mentioned above is substantially the D-J type fuel injection system.

Next, functional operation of the electronic controller 40 for the control of air-fuel ratio is described below. At least, on the basis of the value outputted from the negative-pressure sensor 48 and the number of the rotation of the engine detected by the crank-angle sensor 32, central processing unit (CPU) 56 of the electronic controller 40 computes the basic injecting pulse time. The CPU 56 executes correction and transitory correction of the basic injecting pulse time and feedback correction of the value from the A/F ratio detection device 31, and finally determines the quantity of fuel to be supplied from the fuel-injection valve 41 in order that it can correctly match the objective air-fuel ratio.

Figure 3:
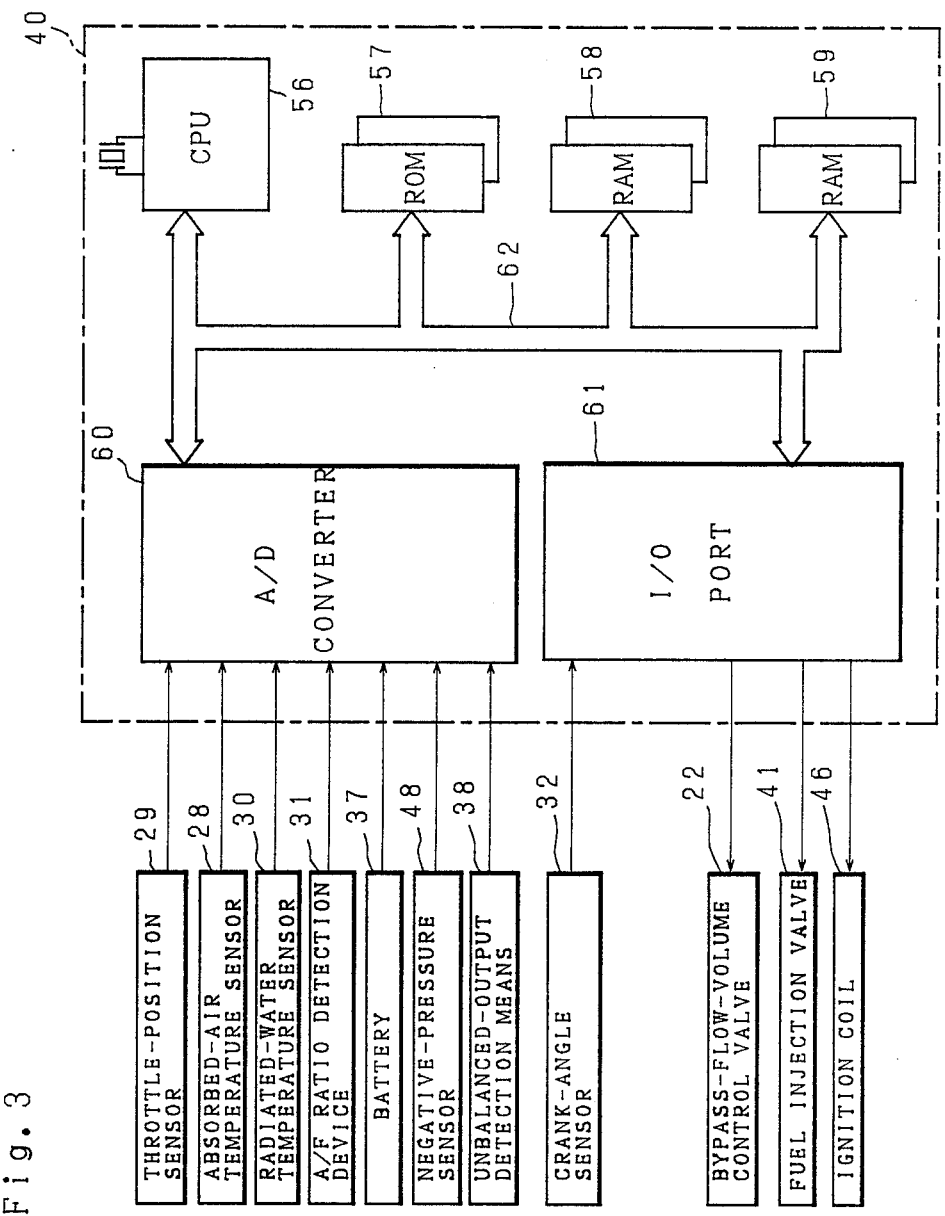
FIG. 3 is a schematic block diagram of the electronic controller according to the invention.

FIG. 3 is a detailed block diagram of the electronic controller 40. The CPU 56 executes a variety of computations and control operations. ROM 57 stores correction programs (to be described later on) and those programs needed for controlling bypass flow quantity. RAM 58 provisionally stores those data under computation. The second RAM 59 composed of non-volatile storage elements securely retains essential data by constantly receiving auxiliary power even when the engine remains OFF. Analog-digital (A/D) converter 60 converts the analog signal into a digital signal. I/O port 61 outputs and receives data to and from external sources. Bus 62 transfers data to each constituent of the electronic controller 40. Signals outputted from throttle-position sensor 29, negative-pressure sensor 48, absorbed-air temperature sensor 28, radiated-water temperature sensor 30, unbalanced-output detection means 38, A/F ratio detection device 31, and battery 37, are respectively delivered to A/D converter 60. Signals outputted from crank-angle sensor 32 and engine-rotation number sensor 32 are respectively delivered to I/O port 61. Bypass quantity control valve 22, fuel injection valve 41, and ignition coil 46 respectively receive signals from CPU 56 through I/O port 61.

Next, an example of controlling function of the fuel-supply device is described below. The fuel-supply device is properly controlled by the electronic controller 40 which computes the objective air-fuel ratio, corrects this ratio, and controls the function of the fuel-supply device so that the corrected objective value of air-fuel ratio can be maintained. ROM 57 stores the processing programs.

Figure 4:
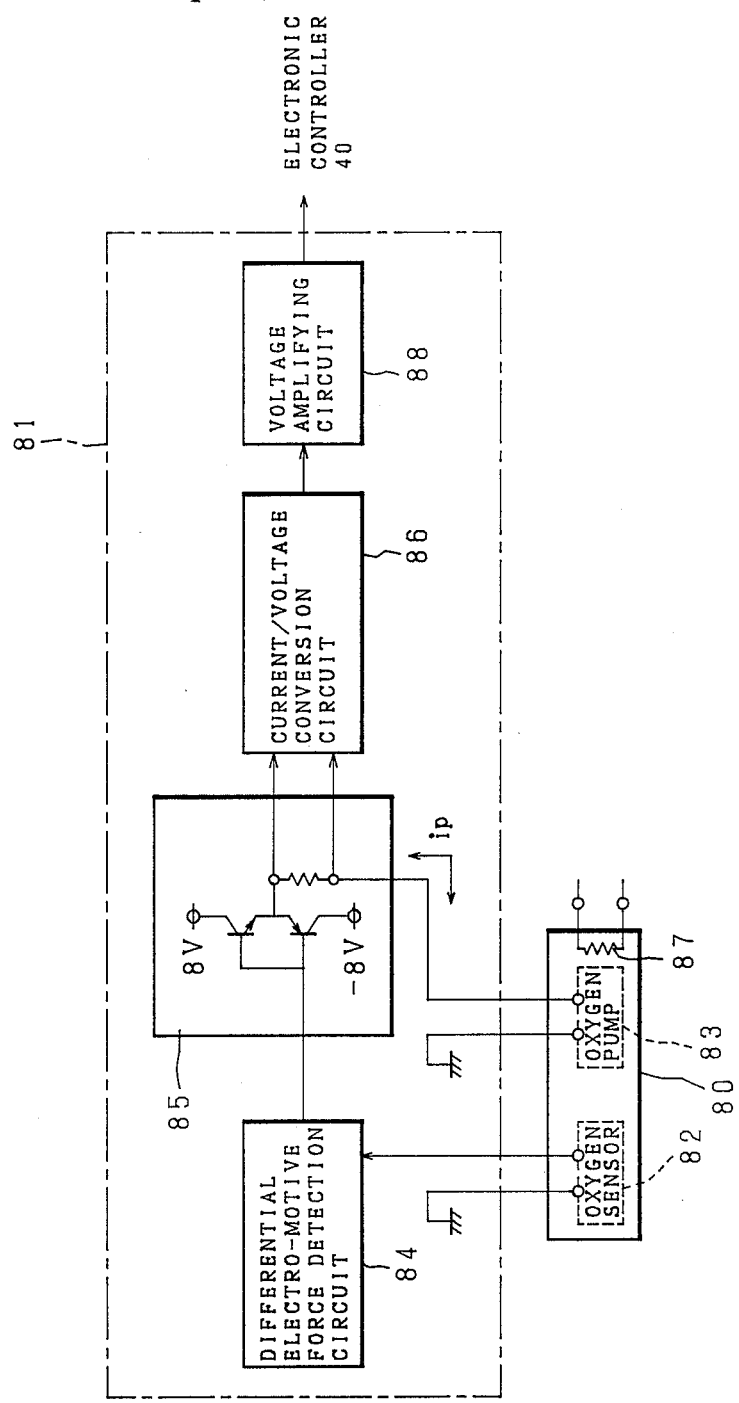
FIG. 4 is a simplified block diagram of the air-fuel ratio detection device of the air-fuel ratio controller according to the invention.

FIG. 4 is a schematic block diagram of the A/F ratio detection device 31 which is composed of wide-range A/F ratio sensor 80 and A/F ratio detection circuit 81. The wide-range A/F ratio sensor 80 is composed of the following: solid electrolyte oxygen sensor 82 which generates an electromotive force responsive to the difference of oxygen concentration between atmosphere and exhaust gas of the engine, solid electrolyte oxygen pump 83 which allows pump current flow in order that the voltage outputted from the solid electrolyte oxygen sensor 82 can be stabilized at a predetermined value, and heater 87 which heats both the oxygen sensor 82 and oxygen pump 83 for activating these. The A/F ratio detection circuit 81 is composed of circuit 84 which detects value of the differential electromotive force generated by oxygen sensor 82, circuit 85 which feeds pump current $i_P$, current/voltage conversion circuit 86, and voltage amplifying circuit 88.

Next, functional operation of the A/F ratio detection device 31 is described below. The differential electromotive force detection circuit 84 detects the difference between the value outputted from the solid electrolyte oxygen sensor 82 and the reference voltage, and then transmits this differential signal to the pump-current supply circuit 85. The pump-current supply circuit 85 then delivers pump current $i_P$ corresponding to the received differential signal to the solid electrolyte oxygen pump 83. As a result, oxygen is supplied, and thus, the signal from the oxygen sensor 82 varies itself to implement a feedback control operation so that the A/F ratio can correctly be the reference value. Concretely, the quantity of oxygen carried by pump current $i_P$ corresponds to the A/F ratio controlled amount. Next, current/voltage conversion circuit 86 converts pump current $i_P$ into a specific voltage. Voltage-amplifying circuit 88 amplifies this voltage and transmits the amplified voltage to the electronic controller 40 as the signal which designates the air-fuel ratio.

Figure 5:
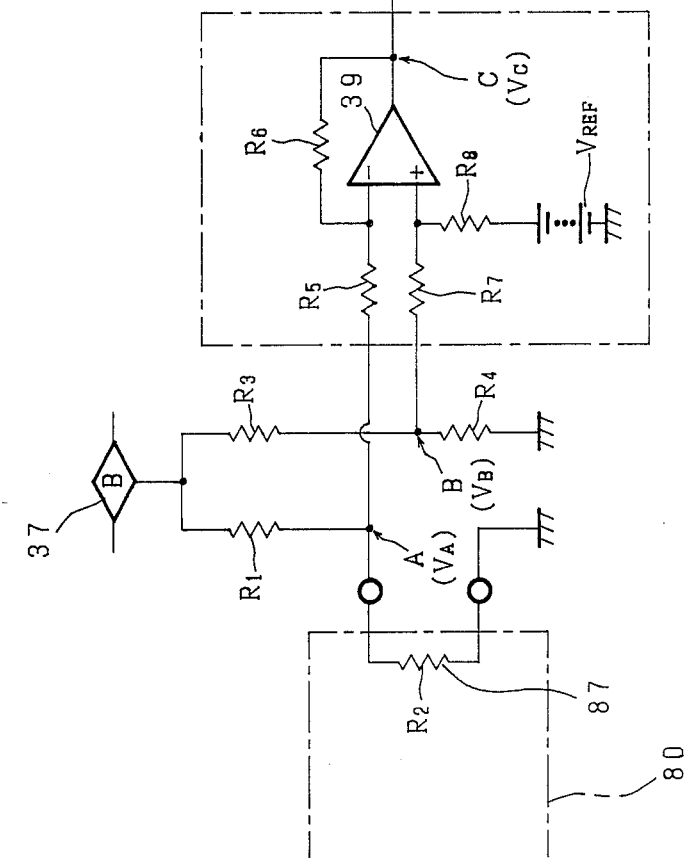
FIG. 5 is a circuit diagram of the heater and unbalance-output detection means according to the invention.

FIG. 5 is a schematic block diagram of the circuit which constitutes means for detecting an abnormal condition of heater 87 of the wide-range A/F ratio sensor 80. Heater 87 having $R_2$ of resistance constitutes a Wheatstone bridge circuit together with resistors $R_1$, $R_3$ and $R_4$, where these are in the relationship of $R_1$, $R_4 = R_2$, $R_3$. Voltages at contacts A and B of $R_1/R_2$ and $R_3/R_4$ are identical to each other. Resistor $R_5$ of unbalanced output detection means 38 is connected to contact A of the Wheatstone bridge circuit, whereas resistor $R_7$ is connected to contact B of this bridge circuit, respectively. Output terminal of resistor $R_5$ is connected to inverted input terminal of operation amplifier 39. The middle of the wire connecting the output terminal of resistor $R_5$ to the inverted input terminal of operation amplifier 39 is connected to the output terminal (contact C) of the amplifier 39. Output terminal of resistor $R_7$ is connected to the non-inverted input terminal of operation amplifier 39. The middle of the wire connecting resistor $R_7$ to the non-inverted input terminal of operation amplifier 39 is connected to the reference-voltage power-supply source $V_{REF}$ via resistor $R_8$, where this power source $V_{REF}$ outputs the reference voltage $V_{REF}$.

Resistors $R_5$ through $R_8$ are respectively provided with a sufficient resistance value which is greater than that is provided for resistors $R_1$ through $R_4$ to prevent resistors $R_1$ through $R_4$ from adversely affecting the amplification rate of the differential amplifier which is composed of operation amplifier 39 and resistors $R_5$ through $R_8$.

Next, functional operation of the CPU 56 for identifying the operating condition of heater 87 is described below. Assume that $R_5=R_6=R_7=R_8=R$. When the heater 87 is properly connected to the abnormal-condition detection circuit shown in FIG. 5, voltage $V_A$ at contact A and voltage $V_B$ at contact B are equal to each other ($V_A=V_B$), and thus, voltage $V_C$ at contact C exactly matches the reference voltage $V_{REF}$ ($V_C=V_{REF}$). If the connector of the heater 87 was incompletely connected to the above circuit or the heater 87 was disconnected from this circuit, then, voltage $V_A$ at contact A becomes the voltage of battery 37. Concretely, this relationship is shown below.

$V_C=V_B-V_A+V_{REF}$, where $V_A>V_B$ and voltage $V_C$ is lower than $V_{REF}$ by $V_A-V_B$.

If, for any reason, the connector of the heater 87 was shorted, then, the voltage relationship becomes $V_C=V_B-V_A+V_{REF}$, where $V_A=0$ and $V_C=V_B+V_{REF}$.

Voltage $V_C$ is delivered to A/D converter 60. If the value including unstable component of resistor $R_2$ is $\Delta V_{REF}$, the CPU 56 identifies that voltage $V_C$ is normal on condition that $V_C$ is within $V_{REF} \pm \Delta V_{REF}$ and voltage $V_C$ is abnormal when $V_C$ is out of this range.

Figure 6:
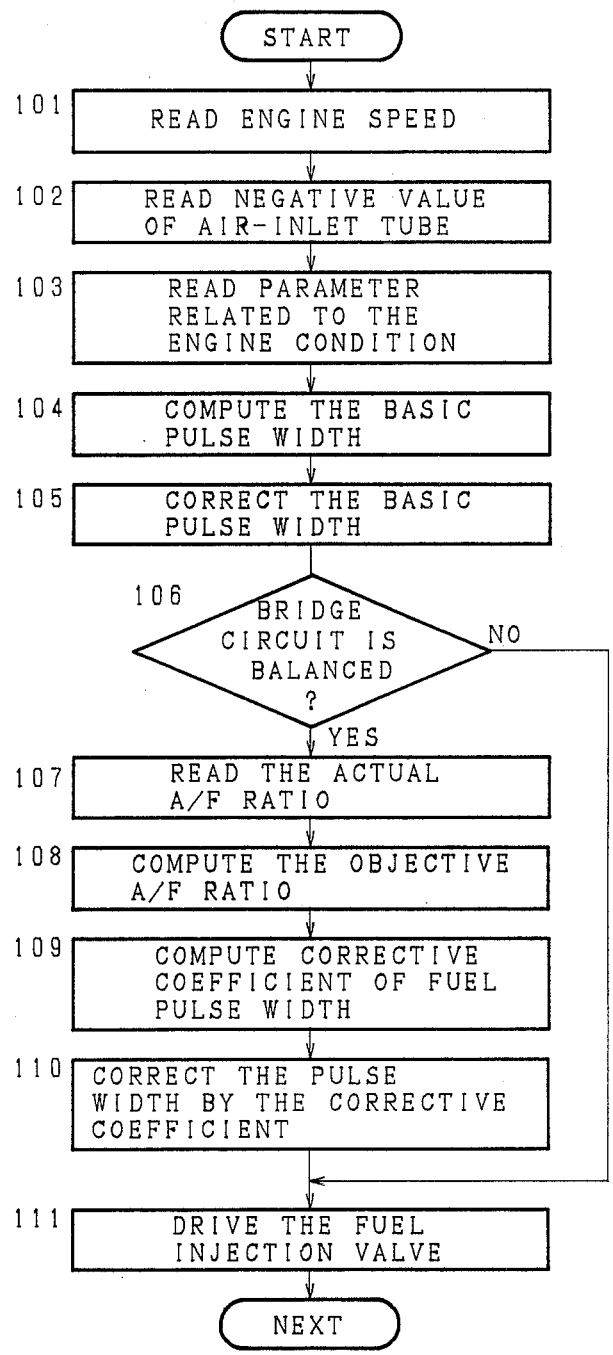
FIG. 6 is a flowchart designating the procedure for controlling the air-fuel ratio according to the invention.

FIG. 6 is a flowchart representing the procedure for controlling the air-fuel ratio embodied by the invention. This procedure is described below. In step 101, the CPU 56 reads the number of the rotation of the engine from the signal outputted from the crank-angle sensor 32, and then, in step 102, the CPU 56 reads the negative value of air-inlet tube from the signal outputted from the negative-pressure sensor 48. Next, in step 103, the CPU 56 reads the parameter related to the engine condition such as radiated-water temperature and temperature of absorbed air. In step 104, the CPU 56 computes the basic pulse width needed for driving the fuel injection valve 41 from the value of the number of the rotation of the engine and the negative pressure of air-inlet tube already read. In step 105, the CPU 56 corrects the basic pulse width by applying values of radiated-water temperature and absorbed-air temperature. Next, in step 106, the CPU 56 identifies whether signals outputted from the Wheatstone bridge circuit are properly balanced or not by referring to the signal outputted from unbalanced output detection means 38. If the above signal is unbalanced, the CPU 56 identifies that the heater 87 is disconnected, and then stops the A/F ratio feedback control so that operation mode can proceed to step 111. When step 111 is underway, the electronic controller 40 drives the fuel injection valve 41 by applying the pulse width computed until processing proceeds to step 105. On the other hand, if the output from the Wheatstone bridge circuit is properly balanced, then the CPU 56 identifies that the heater 87 is functioning correctly. In step 107, the CPU 56 reads the actual A/F ratio from the signal outputted from the A/F ratio detection device 31. Next, in step 108, the CPU 56 computes the objective A/F ratio. In step 109, on the basis of the deviation between the objective and the actual A/F ratios, the CPU 56 computes a corrective coefficient of fuel pulse width. In step 110, the CPU 56 corrects the pulse width by applying the computed corrective coefficient. Finally, in step 111, using the corrected pulse width, the electronic controller drives the fuel injection valve 41.

As this invention may be embodied in several forms without departing from the spirit of essential characteristics thereof, the present embodiment is therefore illustrative and not restrictive, since the scope of the invention is defined by the appended claims rather than by the description preceding them, and all changes that fall within the metes and bounds of the claims, or equivalence of such metes and bounds thereof are therefore intended to be embraced by the claims.

What is claimed is:

1. An air fuel (A/F) ratio controller of an internal combustion engine comprising:

a wide-range A/F ratio sensor which is composed of the following: an oxygen sensor for generating a specific voltage responsive to the difference of oxygen concentration between atmosphere and exhaust gas inside of said internal combustion engine, an oxygen pump for letting pump current flow so that said voltage is a predetermined value, and a heater for heating said oxygen sensor and oxygen pump;

an A/F ratio detection device for detecting A/F ratio of fuel-mixed vapor supplied to said engine in accordance with said pump current;

a controller for executing feedback control of a quantity of fuel to be supplied to said engine so that the detected A/F ratio is an objective value;

abnormal-condition detection means for detecting occurrence of an abnormal condition in said heater on the basis of the resistance value of said heater; and feedback-stop means for stopping said feedback control to said engine when said abnormal condition is detected in said heater, wherein said abnormal-condition detection means of said heater is substantially composed of a Wheatstone bridge circuit which includes said heater, and wherein said means detects whether or not equilibrium of signals outputted from said bridge circuit deviates by more than a predetermined value, and if an unbalance by more than said predetermined value is detected, said means stops execution of feedback control of fuel quantity to be supplied to said engine.

* * * * *